United States Patent [19]

Williams et al.

[11] 4,298,725

[45] Nov. 3, 1981

[54] PROCESS FOR THE PREPARATION OF POLYSACCHARIDE 9

[75] Inventors: Alan G. Williams, Ayr, Scotland; Christopher J. Lawson, Berkshire, England; Julian W. T. Wimpenny, Gwent, Wales

[73] Assignee: Tate & Lyle Limited, England

[21] Appl. No.: 874,201

[22] Filed: Feb. 1, 1978

[51] Int. Cl.³ .......................... C12P 19/04; A23G 3/00
[52] U.S. Cl. ........................................ 536/1; 435/101; 435/253; 435/813; 435/874; 426/658
[58] Field of Search .................. 195/31 P, 96, 115; 536/1; 426/658; 435/101, 813, 874, 253

[56] References Cited

U.S. PATENT DOCUMENTS 3,406,114 10/1968 Goren ........................... 195/31 P X
3,960,832 6/1976 Kung et al. .................... 195/31 P X
3,988,313 10/1976 Bouniot ......................... 195/31 P X

OTHER PUBLICATIONS

Evelergh, "Microbial Monosaccharides and Polysaccharides", *Handbook of Microbiology*, vol. 2, CRC Press, Cleveland, Ohio, Laskin, et al., ed. (1973), pp. 95–96.
Williams, et al., "The Production of an Extracellular Polysaccharide by a *Pseudomonas*-Type Microorganism", *J. Ger. Microbiol*, vol. 77 (1973) XII.
Williams, et al., "Exopolysaccharide Production by *Pseudomonas PBI* in Batch and Continuous Culture: The Effect of Growth Conditions", *J. App. Chem. Biotech.*, vol. 26 (1976), pp. 326–327.
Williams, et al., "Exopolysaccharide Production by Pseudomonans WCIB 11264 Grown in Batch Culture", *J. Gen. Micro.*, vol. 102 (1977), pp. 13–21.

*Primary Examiner*—Thomas G. Wiseman
*Attorney, Agent, or Firm*—Ostrolenk, Faber, Gerb & Soffen

[57] ABSTRACT

A polysaccharide processing useful flow and gel-forming properties is prepared by cultivation of Pseudomonas sp NCIB 11264 (ATCC 31260). The polysaccharide, which readily can be produced in up to 75% yield by continuous culture, possesses properties which are similar to those of xanthan and other gums.

15 Claims, No Drawings

PROCESS FOR THE PREPARATION OF POLYSACCHARIDE 9

This invention relates to a polysaccharide possessing useful flow and gel-forming properties, and to a process for its preparation.

Polysaccharides from microbiological sources are becoming increasingly important in many different industrial applications where materials with particular flow properties are required. Microbial exopolysaccharides can possess unique properties and furthermore can be more easily produced to a uniform specification than plant or algal polysaccharides.

Polysaccharides, such as locust bean gum and alginates, are widely used in industry, as emulsifiers, stabilizers and thickeners. In the food industry, they are used as emulsion stabilizers for ice-cream, as gelling agents for milk puddings, as thickeners for sauces and as foam stabilizers for beer. They are also used in the manufacture of paper and textiles and for thickening drilling muds in oil drilling. Xanthan gums are also increasingly widely used in a range of applications.

We have discovered a polysaccharide possessing in aqueous systems pseudoplastic flow and shear thinning properties which are remarkably similar to those of xanthans and alginates, suggesting similar commercial applications. This polysaccharide can be prepared by cultivating a polysaccharide-producing strain of Pseudomonas sp deposited at the National Collection of Industrial Bacteria, Torry Research Station, 135 Abbey Road, Aberdeen under the Number NCIB 11264, in a nutrient medium therefor. This polysaccharide-producing strain has also been deposited at the American Type Culture Collection in Rockville, Md. under the number ATCC 31260.

Pseudomonas sp NCIB 11264 (ATCC 31260) was isolated from a carbohydrate-rich industrial effluent. Its morphology and physiology may be summarised as follows (all temperatures in degrees centigrade):

Morphology

Oxoid CM3 Nutrient Agar 25°

Gram-negative, small-medium parallel-sided rods, becoming short rods and sometimes coccobacilli.

Motile. Flagella position: single, polar (electron micrographs).

Colonies (6 days): 2 mm, whitish, opaque (translucent confluent growth), circular, entire, low convex, smooth, soft, easily dispersed, no variation.

Physiology 30°

| | |
|---|---|
| Catalase | + |
| Kovacs' oxidase | + |
| Growth at 37° | + (colony growth rate at 37° approximately equal to rate at 25°) |
| Growth at temperatures in excess of 40° | very poor |
| Anaerobic growth, glucose agar | −(slight) |
| Hugh & Leifson Glucose | oxidative |
| Peptone water sugars, Andrades' indicator Glucose, Lactose, Fructose Sucrose, Maltose, Mannitol Glycerol, Starch | no acid |
| Kosers' citrate | + |
| Starch hydrolysis | − |
| King et al A & B | − |
| Arginine, Møllers | − |
| Gelatin hydrolysis | − |
| Casein hydrolysis | − |
| $NH_3$ from tryptone | − |
| $NO_3'$ to $NO_2'$ or $N_2$ | − |
| Christensen'2 urease | alkaline $\leq$ 1½ days |
| DNAse | − |
| Egg yolk plate reaction | − |
| Voges - Proskauer test | − |
| Methyl red | − |
| Indole | − |
| Polypectate degradation | − |

The micro-organism can be cultivated, under aerobic conditions, in any convenient medium in which it will grow and produce exocellular polysaccharide. Typical media include complex broths, e.g. a 1% nutrient broth, or a chemically defined medium such as that described by Gray et al. (Biochimica et Biophysica Acta, 117, 22 32, 1966), with a supplementary carbon source of, for example, glucose or sucrose. A supplement of about 2% w/v in the medium is desirable.

A particularly preferred defined medium (the glucose-supplemented Gray et al medium) for use in the cultivation of Pseudomonas sp NCIB 11264 has the following composition:

| | |
|---|---|
| Glucose | 20 g/liter |
| $NH_4Cl$ | 2.66 g/liter |
| $KH_2PO_4$ | 5.44 g/liter |
| NaOH to pH 7 | approx. 1.5 g/liter |
| solution of trace elements* | 6 ml/liter |

| *a solution containing | | |
|---|---|---|
| | $MgSO_4 . 7H_2O$ | 10 g |
| | $MnCl . 4H_2O$ | 1 g |
| | $FeSO_4 . 7H_2O$ | 0.4 g |
| | $CaCl_2 . 2H_2O$ | 0.1 g |
| | Distilled water to 1 liter | |

The culture may be effected batch-wise or in a continuous manner, according to conventional practice. Continuous cultures are preferably conducted under nitrogen-limiting conditions, e.g. about 0.5 g $NH_4Cl$/liter. With a glucose-supplemented medium, the glucose conversion is about 30% in batch cultures, but up to 75% in continuous cultures.

A temperature of from 25° C. to 35° C. is satisfactory, a temperature of about 30° C. being optimal.

In general, polysaccharide production is found to be enhanced when an excess of carbon source is present, under nitrogen-limited conditions. Preferably the pH of the medium should not fall below 6 and may conveniently be from 6.5 to 8.0.

The exocellular polysaccharide may be isolated from the culture supernatant (free from cells) by precipitation with an organic water-miscible solvent such as isopropoanol and deionized, e.g by a conventional desalting using dialysis. Conveniently, unwanted cellular matter can be removed by trypsin digestion, e.g by digesting an aqueous solution of the polysaccharide buffered to pH 7-8, e.g using 0.2 M HEPES buffer, at about 30° C. in the presence of a bacteriostat such as mercuric chloride. For example, 3.6 liters of solution, buffered to pH 7-8 with 0.2 M HEPES, are treated with 20 mg of the enzyme and mercuric chloride (1.5 ml of a saturated alcoholic solution) for 5 days at 30° C.

After dialysis, the isolated material can be freeze-dried to give the purified dry exopolysaccharide.

Analysis has shown the purified polysaccharide to be a polysaccharide having a repeating unit containing the following components:

7 D-gluco units comprising 1 unit of 6-substituted glucose, 2 units of 4-substituted glucose, 2 units of 3-substituted glucose, and 2 units of 4,6-disubstituted glucose; 1 D-galacto unit comprising 3-substituted galactos; 1 acetate unit; and 1 pyruvate unit; the above components including 1 4,6-disubstituted glucose branch point and 1 side chain terminated by a 4,6-O-(1-carboxyethylidene)-D-glucose unit.

The purified polysaccharide has an optical rotation
$[\alpha]_{22} = -15°$ (C $0.68_{H_2O}$)
which indicates that all the sugars are linked in the $\beta$-D configuration.

The viscosity and flow properties of the polysaccharide of the present invention may be described in terms of the consistency index k and the flow behaviour index n, as suggested by Krumel and Sarkar, "Flow Properties of Gums useful in the Food Industry", in Food Technology, April 1975 pp 36–44, Vol. 29(4).

The apparent viscosity ($\eta$) in centipoises was measured using a cone and plate viscometer at various rates of shear (D) in $\sec^{-1}$. A plot of log $\eta$ against log D for a 1% by weight solution of the polysaccharide according to the present invention at 25° C. gave a straight line graph which gave a k value ($\eta$ extrapolated to a shear rate of 1 $\sec^{-1}$) of 4600 cps and an n value (the slope of the graph plus 1) of 0.22. A commercial sample of food grade xanthan gum sold under the Trade Mark Keltrol by Kelco of San Diego, California gave under the same conditions values of k and n of 5,000 and 0.23 respectively.

The following Examples illustrate the invention:

EXAMPLE 1

10 Liter Batch Fermentation

Exopolysaccharide production by Pseudomonas sp NCIB 11264 was followed in a 10 liter batch fermentation, without pH control, for 50 hours at 30° with volume/volume aeration and an impeller speed of 350 rpm. The doubling time of the organism under these conditions was 140 minutes.

Logarithmic growth continued for some 18 hours at which point ($E_{520}$ 6.0) all nutrients were apparently in excess, although the oxygen tensions were not determined. It is known, however, that exopolysaccharide synthesis is at a maximum when the oxygen tension is non-limiting. At this stage, polysaccharide could be detected by isopropanol precipitation, although exopolymer had been detectable in increasing amounts in culture supernatants from 12–13 hours after inoculation utilising a more sensitive viscometric assay. Thus, although exopolysaccharide production apparently commenced during the late exponential phase of growth, the formation was maintained maximally for another 20 hours during the stationary growth phase, before the rate of production eventually began to decrease. This fermentation pattern is typical of a secondary metabolite.

Of the glucose utilised, only 30% was converted into exopolysaccharide the other 70% being metabolised to establish and maintain the culture.

EXAMPLE 2

Steady State Exopolysaccharide Production

Exopolysaccharide-producing cultures of Pseudomonas sp NCIB 11264 were maintained in a steady state for up to 500 hours. The defined medium based on that described by Gray et al (1966) supplemented with glucose (10 mg/ml), was used in all the previously described continuous culture studies.

As a result of these investigations, the initial concentrations of some of the components were reduced, and continuous polymer production followed under conditions of imposed nitrogen limitation. Conditions were optimised at pH 7.0±0.1 with a growth temperature of 30°±1° and an aeration rate of 500 ml/min.

After inoculation, the culture was grown as a batch and allowed to establish for 24 hours before the flow rate was adjusted to 44 ml/hour. The course of the fermentation, run at a dilution rate of 0.08 $hr^{-1}$, was followed for 500 hours. An impeller speed of 900±10 rpm was maintained throughout. Steady state values for total cell density, polysaccharide level and glucose conversion remained constant—after 100 hrs these values were respectively 0.26 ($E_{520} \times 10^{-1}$), 1.6 mg/ml and 40%, while after 500 hours they were 0.26 ($E_{520} \times 10^{-1}$), 1.6 mg/ml and 45%. There was no evidence to indicate cultural deterioration or development of mutant strains.

Polysaccharide samples analaysed were of a constant composition and solutions of the polymer (0.1 mg/ml) had a similar relative viscosity (1.7±0.05) when measured at 25° with a modified Zimm-Crothers rotating cylinder type viscometer (55 mA), indicating that there had been no change in the molecular weight of the exopolymer produced over the period of the fermentation.

We claim:

1. A process for the preparation of a polysaccharide which comprises cultivating Pseudomonas sp NCIB 11264 (ATCC 31260) to yield an exocellular polysaccharide.

2. The process of claim 1 wherein cultivation is effected in a continuous manner.

3. The process of claim 2 wherein the cultivation in a continuous manner is conducted under nitrogen-limited conditions.

4. The process of claim 2 wherein the cultivation is effected in a cultivation medium comprising $NH_4Cl$ and $KH_2PO_4$ supplemented with a supplementary carbon source.

5. The process of claim 4 wherein the cultivation medium is supplemented with glucose or sucrose.

6. The process of claim 1 wherein the cultivation is effected at 25° C. to 35° C.

7. The process according to claim 1 wherein the pH of the cultivation medium is maintained at above 6.

8. The process according to claim 7 wherein said pH is maintained at 6.5 to 8.

9. The process of claim 1 wherein the exocellular polysaccharide is isolated by precipitation with an organic water-miscible solvent and is then deionised.

10. The process of claim 9, wherein the isolated polysaccharide is freeze-dried.

11. The process of claim 1 wherein said exocellular polysaccharide is recovered.

12. A process for the preparation of an exocellular polysaccharide which process consists essentially of the steps of:

(a) inoculating a nutrient medium with Pseudomonas sp NCIB 11264 (ATCC 31260);

(b) cultivating said Pseudomonas sp NCIB 11264 (ATCC 31260) until a substantial formation occurs of an exocellular polysaccharide; and (c) recovering said exocellular polysaccharide from said nutrient medium.

13. The process of claim 12 wherein the step of cultivating said Pseudomonas sp NCIB 11264 (ATCC 31260) is effected in a continuous manner under nitrogen-limited conditions at 25° C. to 35° C. in a cultivation medium $NH_4Cl$ and $KH_2PO_4$ supplemented with a supplementary carbon source while maintaining the pH of the cultivation medium at above 6.

14. The process of claim 12 wherein the step of recovering said exocellular polysaccharide comprises precipitating the polysaccharide with an organic mater-miscible solvent, and then deionising and freeze-drying said polysaccharide.

15. A polysaccharide produced by Pseudomonas sp. NCIB 11264 characterized by an optical rotation $[\alpha]_{22}$ of $-15°$ C. (c $0.68_{H_2O}$), an apparent viscosity of 4,600 cps measured at 25° C. for a one percent by weight solution, and a repeating unit which has one side chain terminated by a 4,6-O-(1-carboxyethylidene)-D-glucose and one 4,6 disubstituted glucose branch point, wherein the repeating unit comprises an acetate, a pyruvate, a 3-substituted-D-galactose, and 7 glucoses comprising a 6-substituted glucose, two 4-substituted glucoses, two 3-substituted glucoses and two 4,6-disubstituted glucoses, one of which is said branch point.

* * * * *